(12) United States Patent
Jun (10) Patent No.: US 11,105,755 B2
(45) Date of Patent: Aug. 31, 2021

(54) X-RAY DETECTING PANEL FOR MULTI SIGNAL DETECTION AND X-RAY DETECTOR THEREOF

(71) Applicant: BIOSENSTECH INC., Yongin (KR)

(72) Inventor: Seung Ik Jun, Frisco, TX (US)

(73) Assignee: BIOSENSTECH INC, Yongin (KR)

( * ) Notice: Subject to any disclaimer, the term of this patent is extended or adjusted under 35 U.S.C. 154(b) by 117 days.

(21) Appl. No.: 16/453,787

(22) Filed: Jun. 26, 2019

(65) Prior Publication Data

US 2020/0408703 A1    Dec. 31, 2020

(51) Int. Cl.
| | | |
|---|---|---|
| *G01N 23/04* | (2018.01) | |
| *A61B 6/00* | (2006.01) | |
| *G01T 1/24* | (2006.01) | |

(52) U.S. Cl.
CPC ......... *G01N 23/04* (2013.01); *A61B 6/4241* (2013.01); *A61B 6/482* (2013.01); *G01T 1/247* (2013.01); *G01N 2223/413* (2013.01); *G01N 2223/423* (2013.01)

(58) Field of Classification Search
CPC ......... G01T 1/1603; G01T 1/242; G01T 1/16; G01T 1/247; G01N 2223/423; G01S 15/8909
See application file for complete search history.

(56) References Cited

U.S. PATENT DOCUMENTS

| | | | | |
|---|---|---|---|---|
| 7,742,119 B2* | 6/2010 | Lin | .................... | G02F 1/136259 |
| | | | | 349/55 |
| 2010/0051820 A1* | 3/2010 | Okada | ................... | G01T 1/2018 |
| | | | | 250/370.09 |
| 2012/0161020 A1* | 6/2012 | Ryu | ......................... | G01T 1/24 |
| | | | | 250/370.14 |
| 2012/0181439 A1* | 7/2012 | Cao | ........................ | H04N 5/335 |
| | | | | 250/366 |
| 2013/0168563 A1* | 7/2013 | Kim | ........................ | G01T 1/16 |
| | | | | 250/370.06 |
| 2014/0166888 A1* | 6/2014 | Lu | ..................... | H01L 27/14634 |
| | | | | 250/366 |
| 2016/0284748 A1* | 9/2016 | Mruthyunjaya | .. | H01L 27/14692 |
| 2018/0061884 A1* | 3/2018 | Jun | ................... | H01L 27/14627 |

FOREIGN PATENT DOCUMENTS

| | | |
|---|---|---|
| JP | 2002350551 A | 12/2002 |
| KR | 20150043630 A | 4/2015 |
| KR | 101669434 A | 10/2016 |
| KR | 101678671 B1 | 11/2016 |

* cited by examiner

*Primary Examiner* — Yara B Green (57) ABSTRACT

An X-ray detecting panel for multi signal detection and an X-ray detector thereof are disclosed. In accordance with one embodiment, the X-ray detecting panel for multi signal detection may include a plurality of unit pixels, the unit pixel including: a photodiode for generating an electrical signal by radiated light; and a thin film transistor for processing the electrical signal generated in the photodiode, wherein the unit pixel may include at least two photodiodes or at least two thin film transistors. In accordance with the present embodiment, a plurality of photodiodes is provided in the unit pixel in a single X-ray detector, thus it is possible that an X-ray image is output using a signal output from each photodiode, and multi signals are detected using the single X-ray detector.

17 Claims, 7 Drawing Sheets

X-RAY DETECTING PANEL FOR MULTI SIGNAL DETECTION AND X-RAY DETECTOR THEREOF

TECHNICAL FIELD

Exemplary embodiments of the present disclosure relate to an X-ray detecting panel for multi signal detection and an X-ray detector thereof, and more particularly to an X-ray detecting panel for multi signal detection and an X-ray detector thereof, which can detect multi signals using a single X-ray source and a single X-ray detector.

BACKGROUND

X-rays are electromagnetic waves, and because of their relatively short wavelength and large energy compared to visible light, they easily pass through matter. Since the transmittance of X-rays differs depending on the densities of materials and types of atoms, a difference in contrast may occur when X-rays are transmitted. When the actual x-rays are radiated onto a human body, the transmittance of the X-rays differs between bones having high density and organs or tumors having low density, and accordingly, the contrast can be displayed on the x-ray image.

Figure 1A:
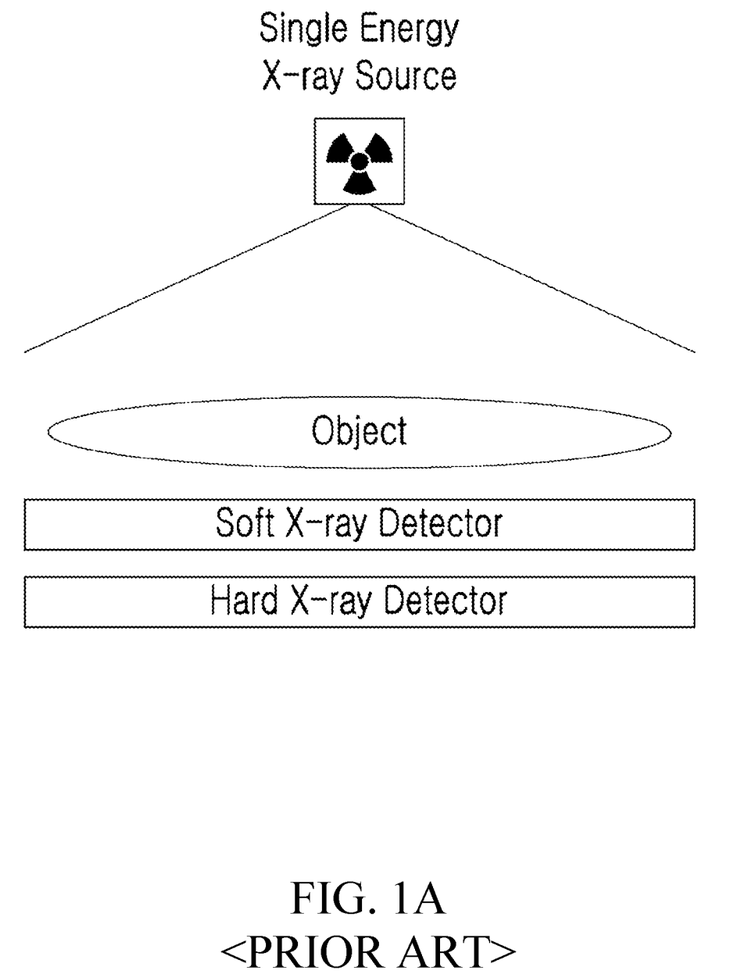
FIG. 1A is a schematic view illustrating an X-ray detector using a conventional single X-ray source.

As shown in FIG. 1A, when an X-ray source and an X-ray detector commonly used at present are intended to simultaneously realize images of bones with relatively dense densities and soft tissues that are not so dense, X-rays are radiated at a relatively high dose to bones, and X-rays are radiated at relatively low dose to soft tissues to detect images. That is, an object such as a human body is radiated twice with X-rays using a single X-ray source; X-rays are radiated to soft tissues and bones, and X-rays are detected and images are acquired through a soft X-ray detector and a hard X-ray detector, respectively.

Figure 1B:
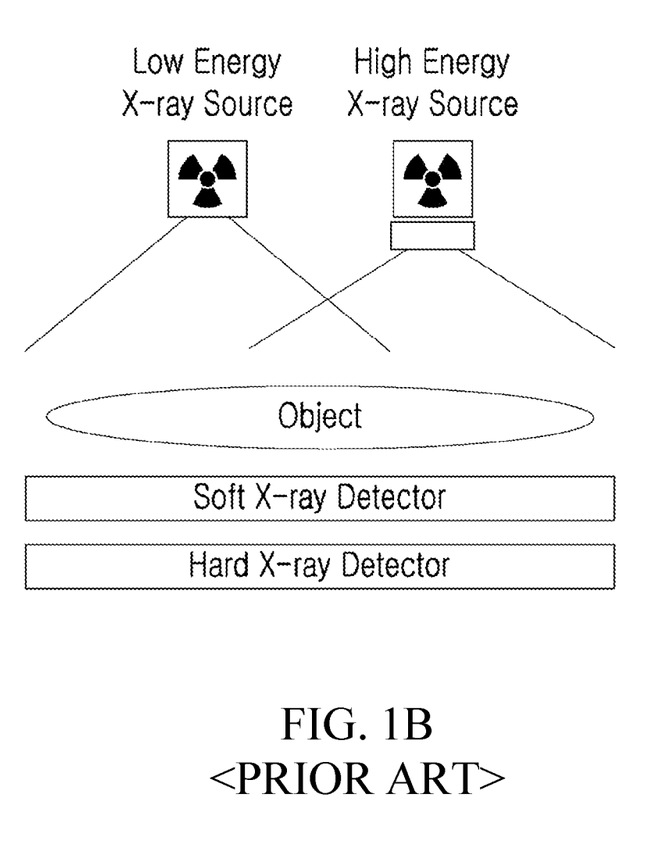
FIG. 1B is a schematic view illustrating an X-ray detector using conventional multiple X-ray sources.

And if X-ray images of bones and soft tissues are intended to be realized at the same time, the images are realized using multiple X-ray sources and multiple X-ray detectors as illustrated in FIG. 1B because it is not easy to realize them using the single X-ray source.

Meanwhile, an industrial X-ray detector can be used, for example, in inspecting defective printed circuit boards. In this case, main materials of the printed circuit board are lead, copper, and plastic. When photographing the printed circuit board with a typical X-ray dose, a difference in contrast between lead and non-lead portions is significant (roughly 20 times), so a higher dose of X-rays should be applied to inspect a thickness of the lead or an internal defect in the lead. However, when radiating a high dose of X-ray to inspect the inside of the lead, it is not relatively easy to acquire an image of copper or plastic. Thus, there is a problem in that it is not easy that a single X-ray source is used to simultaneously acquire image information on the printed circuit board.

Therefore, since it is difficult for a conventional X-ray detector to acquire X-ray images of the human body or an industrial object having various densities, the conventional X-ray detector realizes the image using the multiple X-ray sources and the multiple X-ray detectors as shown in FIG. 1B.

As described above, when using the conventional multiple X-ray sources and multiple X-ray detectors, there are problems in that its configuration is complex, the size of the entire equipment increases, and the cost of its use increases.

Examples of the background techniques are disclosed in Korean Patent Laid-Open Publication No. 10-2015-0043630, published on Apr. 23, 2015 and Korean Patent Registration No. 10-1669434, registered on Oct. 20, 2016.

SUMMARY

Exemplary embodiments of the present disclosure provide an X-ray detecting panel for multi signal detection and an X-ray detector thereof, which can obtain a normal X-ray image even when X-rays are radiated using a single X-ray source for an object that requires relatively different X-ray doses.

In accordance with one aspect of the present disclosure, an X-ray detecting panel for multi signal detection includes a plurality of unit pixels, the unit pixel including: a photodiode for generating an electrical signal by radiated light; and a thin film transistor for processing the electrical signal generated in the photodiode, wherein the unit pixel includes at least two photodiodes or at least two thin film transistors.

In one embodiment, the unit pixel may include at least two photodiodes, and the at least two photodiodes may have different photoelectric properties each other.

The at least two photodiodes may have different materials and thicknesses each other, or may have different fill factors each other.

In one embodiment, the unit pixel may include a single thin film transistor, and each of the at least two photodiodes may be electrically connected to a bias line at one side and electrically connected to a source terminal of the thin film transistor at the other side, wherein a drain terminal of the thin film transistor may be connected to a readout so as to output a signal generated in the at least two photodiodes as image information.

In another embodiment, the unit pixel may include at least two thin film transistors, wherein the at least two thin film transistors may have different electrical characteristics each other.

The at least two thin film transistors may be configured to have different channel resistances, on-currents, off-currents, channel lengths, channel widths, or threshold voltages from each other.

In one embodiment, one sides of the at least two photodiodes may be electrically connected to a bias line, and other sides of the at least two photodiodes may be electrically connected to source terminals of the at least two thin film transistors, respectively, and wherein drain terminals of the at least two thin film transistors may be connected to at least two readouts so as to output a signal generated in each of the at least two photodiodes as image information.

In another embodiment, the unit pixel may include a single photodiode, the photodiode having one side electrically connected to a bias line and the other side electrically connected to source terminals of the at least two thin films transistors, wherein drain terminals of the at least two thin film transistors may be connected to at least two readouts so as to output signals generated in the photodiode as image information.

In accordance with one aspect of the present disclosure, an X-ray detecting panel for multi signal detection includes a plurality of unit pixels, the unit pixel including: a first thin film transistor directly detecting radiated X-rays as an electrical signal and processing the detected electrical signal; and a second thin film transistor directly detecting the radiated X-rays as an electrical signal and processing the detected electrical signal, wherein the first and second thin film transistors may have different electrical characteristics each other.

The first and second thin film transistors may be configured to have different channel resistances, on-currents, off-currents, channel lengths, channel widths, or threshold voltages from each other.

Source terminals of the first and second thin film transistors may be electrically connected to a common line where X-rays are detected as electrical signals, and drain terminals of the first and second thin film transistors may be connected to first and second readouts to output electrical signals in which X-rays are detected as image information.

In accordance with one aspect of the present disclosure, an X-ray detector for multi signal detection includes an X-ray detecting panel for multi signal detection including a plurality of unit pixels, the unit pixel including: a photodiode generating an electrical signal by radiated light; and a thin film transistor processing the electrical signal generated in the photodiode, wherein the unit pixel includes at least two photodiodes or at least two thin film transistors.

Further, the unit pixel may include at least two photodiodes having different photoelectric characteristics each other. For example, the at least two photodiodes may have different materials and thicknesses each other, or may have different fill factors each other.

Each of the at least two photodiodes may be electrically connected to a bias line at one side and to a source terminal of the thin film transistor at the other side, wherein a drain terminal of the thin film transistor may be connected to a readout so as to output a signal generated in the at least two photodiodes as image information.

The unit pixel may include at least two thin film transistors, wherein one side of the at least two photodiodes may be electrically connected to a bias line, and other sides of the at least two photodiodes may be electrically connected to source terminals of the at least two thin film transistors, respectively, and wherein drain terminals of the at least two thin film transistors may be connected to at least two readouts so as to output a signal generated in each of the at least two photodiodes as image information.

Meanwhile, the unit pixel may include at least two thin film transistors, wherein the at least two thin film transistors may be configured to have different channel resistances, on-currents, off-currents, channel lengths, channel widths, or threshold voltages from each other.

In accordance with one aspect of the present disclosure, an X-ray detector for multi signal detection includes an X-ray detecting panel for multi signal detection including a plurality of unit pixels, the unit pixel including: a first thin film transistor directly detecting radiated X-rays as an electrical signal and processing the detected electrical signal; and a second thin film transistor directly detecting the radiated X-rays as an electrical signal and processing the detected electrical signal, wherein the first and second thin film transistors may have different electrical characteristics each other.

In accordance with embodiments of the present disclosure, a plurality of photodiodes or a plurality of thin film transistors are provided in a unit pixel in the X-ray detector, so that multi signals can be detected using a single X-ray detector.

Moreover, a plurality of thin film transistors having different electrical characteristics each other are provided in a unit pixel of a detecting panel capable of directly detecting an X-ray as an electrical signal, and thus there is an effect that multi signals can be detected through signals output by these thin film transistors.

BRIEF DESCRIPTION OF THE DRAWINGS

The accompanying drawings, which are included to provide a further understanding of the disclosed technology, and are incorporated in and constitute a part of this specification, illustrate exemplary embodiments of the disclosed technology, and together with the description serve to describe the principles of the disclosed technology.

DETAILED DESCRIPTION

Figure 2:
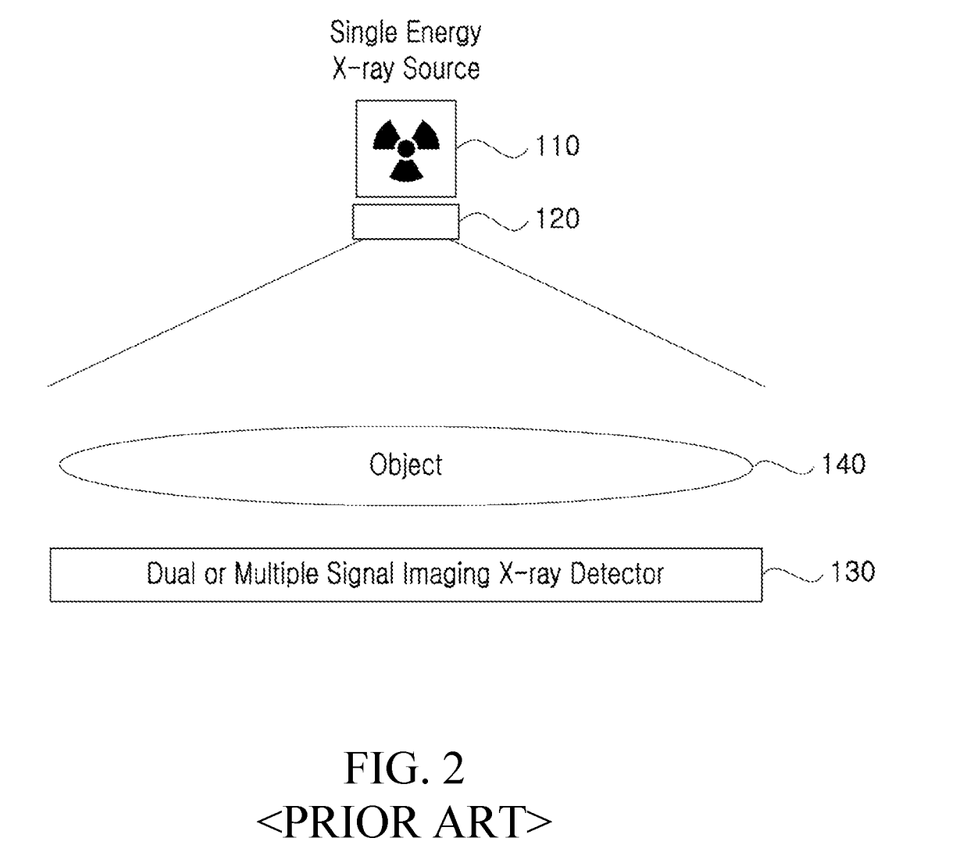
FIG. 2 is a schematic view illustrating a single X-ray detector using a single X-ray source according to an embodiment of the present disclosure.

Hereinafter, exemplary embodiments of the present disclosure will be described in detail with reference to the accompanying drawings FIG. 2 is a schematic view illustrating a single X-ray detector using a single X-ray source according to an embodiment of the present disclosure.

Referring to FIG. 2, in accordance with one embodiment of the present disclosure, a single X-ray detector 130 using a single X-ray source includes an X-ray source 110, a filter 120, and the X-ray detector 130.

The X-ray source 110 is an X-ray generator generating and radiating X-rays, and one X-ray source 110 may be provided in this embodiment. In this embodiment, the X-ray source 110 may radiate X-rays having a predetermined energy band. The energy band of radiated X-rays may have a predetermined range, and the filter 120 may be installed in a direction in which the X-ray is radiated.

The filter 120 is disposed to adjust the energy of the X-rays radiated from the X-ray source 110, and may filter X-rays of a particular energy band. The filter 120 may be an additional filter. In this case, a maximum energy radiated from the X-ray source 110 may be controlled by the magnitude of the voltage, and a minimum energy may be controlled by the filter 120. By controlling the minimum energy of the X-rays using the filter 120, an average energy of the radiated X-rays may be increased. In this embodiment, the filter 120 may be the filter 120 formed of a metal such as copper (Cu). Accordingly, this may result in hardening of a beam quality of X-rays to increase the energy band range, and also reducing an exposure dose of an object 140.

The X-ray detector 130, in one embodiment of the present disclosure, may detect dual or multi signals and may be configured as in many embodiments described below.

In the present embodiment, the X-ray detector 130 may be a direct type X-ray detector which directly detects X-rays as electrical signals and an indirect type X-ray detector which converts X-rays into the visible light and detects it using the converted visible light.

In the direct and indirect type X-ray detectors as described above, the X-ray detecting panel included in the X-ray detector 130 may include a large number of image pixels to convert the X-rays into electrical signals. Therefore, in the following embodiments, configurations in each unit pixel will be described in detail.

Figure 3:
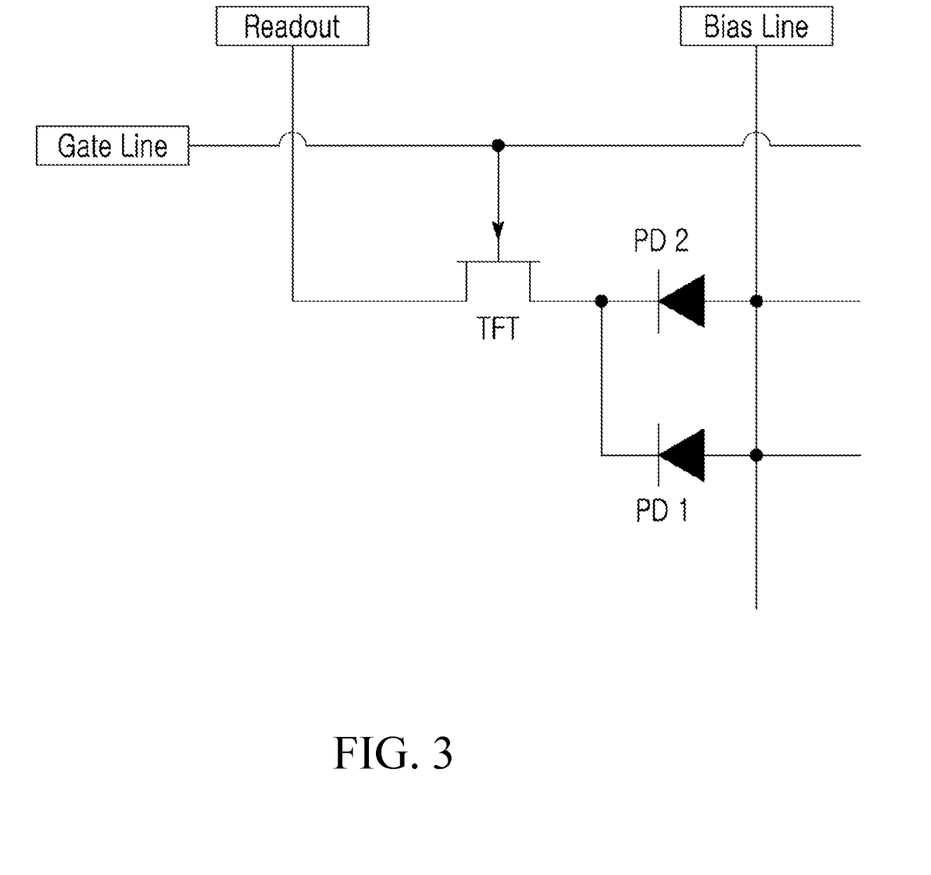
FIG. 3 is a pixel circuit diagram illustrating a single X-ray detector according to a first embodiment of the present disclosure.

FIG. 3 is a circuit diagram illustrating a single X-ray detector according to a first embodiment of the present disclosure.

Referring to FIG. 3, in accordance with the first embodiment of the present disclosure, a single X-ray detector 130 may include one thin film transistor TFT and two photodiodes PD1 and PD2 in a single unit pixel.

In this embodiment, the unit pixel as described above may be included in an X-ray detecting panel of the X-ray detector 130, and may detect X-rays and output a signal.

The two photodiodes PD1 and PD2 may have the same photoelectric characteristics each other, but the present disclosure is not limited thereto. In particular, in this embodiment, the two photodiodes PD1 and PD2 may be configured to have different photoelectric characteristics.

The two photodiodes PD1 and PD2 having different photoelectric characteristics each other may be formed of different materials or thicknesses each other so as to generate an electrical signal from radiated light, or may be configured to have different fill factors each other. In this case, a PIN diode, an avalanche photo diode APD, or the like may be respectively used as the photodiodes PD1 and PD2 in this embodiment.

In this embodiment, each of the two photodiodes PD1 and PD2 may be electrically connected to a bias line at one side, and may be connected a source terminal of the thin film transistor TFT at the other side, respectively. A gate terminal of the thin film transistor TFT may be connected to a gate line, and a drain terminal of the thin film transistor TFT may be connected to a readout.

Accordingly, a signal output from the thin film transistor TFT may be extracted through a readout terminal and may be realized as an image through an external electronic device connected to the readout terminal.

In this embodiment, X-rays emitted from the X-ray source 110 may be converted into visible light and radiated onto the two photodiodes PD1 and PD2, respectively, wherein the two photodiodes PD1 and PD2 may generate different electrical signals from the radiated visible light through different photoelectric properties each other. Therefore, each electrical signal output from the two photodiodes PD1 and PD2 may be processed by each of thin film transistors and realized as a different image, respectively. Accordingly, even when the same X-rays are radiated to the object 140 by using one X-ray source 110, an image having sharper contrast with respect to the object 140 may be realized depending on the photoelectric characteristics that can be detected in the two photodiodes PD1 and PD2.

In this embodiment, although two photodiodes PD1 and PD2 are used, more photodiodes may be included in one pixel if necessary.

Figure 4:
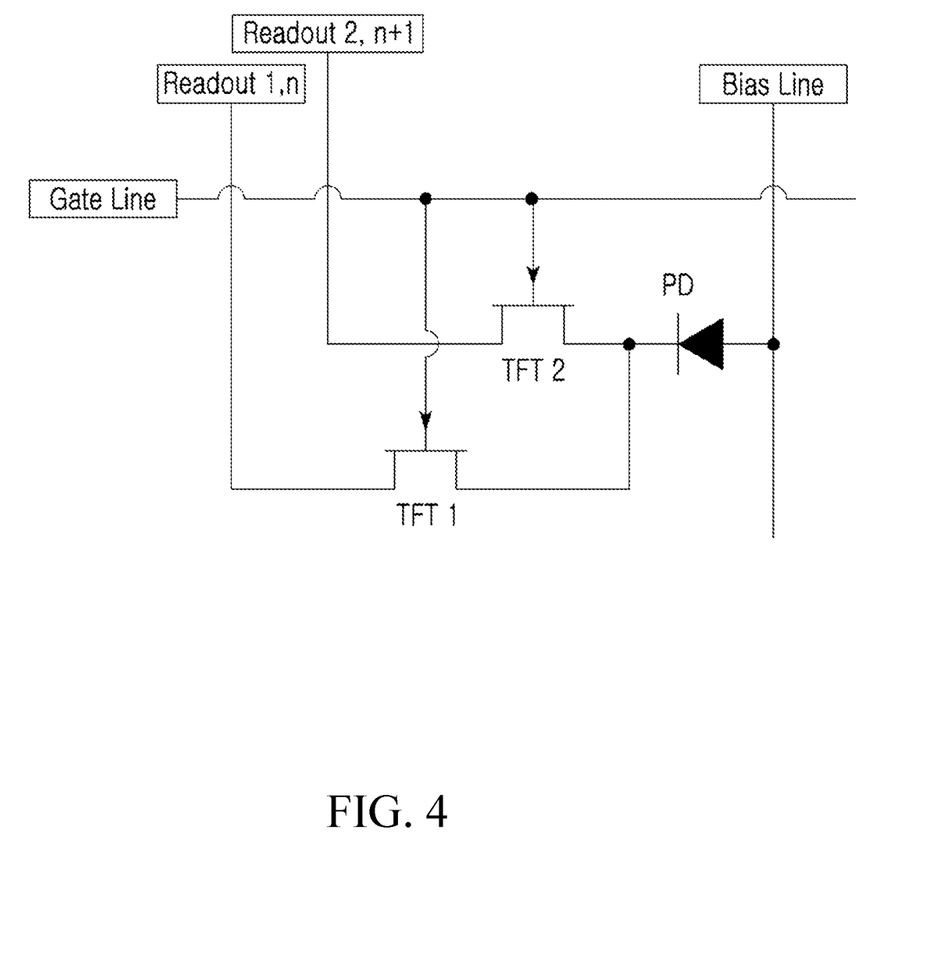
FIG. 4 is a pixel circuit diagram illustrating a single X-ray detector according to a second embodiment of the present disclosure.

FIG. 4 is a circuit diagram illustrating a single X-ray detector according to a second embodiment of the present disclosure.

Referring to FIG. 4, in accordance with the second embodiment of the present disclosure, a single X-ray detector 130 may include two thin film transistors TFT1 and TFT2 and one photodiode PD in a single unit pixel. The two thin film transistors TFT1 and TFT2 may have the same electrical characteristics, but the present disclosure is not limited thereto, and may have different electrical characteristics each other. The unit pixel such as above may be included in an X-ray detecting panel of the X-ray detector 130, and may detect X-rays and output a signal For example, each of the two thin film transistors TFT1 and TFT2 may be configured to have a different channel resistance, a different on-current, a different off-current, a different channel length, a different channel width, and a different threshold voltage so as to process signals generated in the photodiode PD.

In this embodiment, the photodiode PD may be electrically connected to a bias line at one side and may be connected to source terminals of the two thin film transistors TFT 1 and TFT 2 at the other side. Gate terminals of the two thin film transistors TFT1 and TFT2 may be connected to a gate line and drain terminals of the two thin film transistors TFT1 and TFT2 may be connected to two readouts Readout1 and Readout2. Each of readout signals generated in the two thin film transistors TFT1 and TFT2 may be extracted through each readout terminal and may be realized as an image through an external electronic device connected to the readout terminals.

In this embodiment, X-rays emitted from the X-ray source 110 may be converted into visible light and radiated onto the photodiode PD, and electrical signals from the radiated visible light through different photoelectric properties may be generated. The electrical signals output from the photodiode PD in the two thin film transistors TFT1 and TFT2 may be respectively processed by using the electrical characteristics of the two thin film transistors TFT1 and TFT2 to realize different images each other. Therefore, even when the same X-rays are radiated to the object 140 using one X-ray source 110, it is possible to realize an image having a sharper contrast with respect to the object 140 since the electric characteristics processed by the two thin film transistors TFT1 and TFT2 are different.

In this embodiment, although two thin film transistors TFT1 and TFT2 are used, more thin film transistors may be included in one pixel if necessary.

Figure 5:
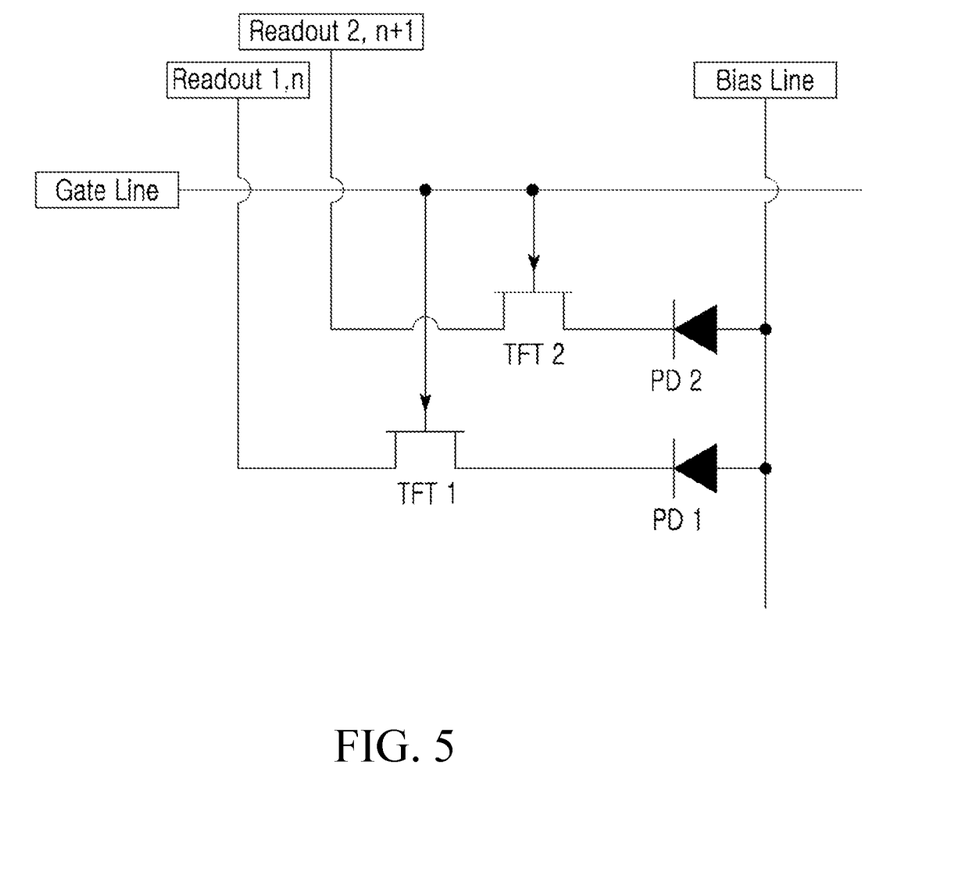
FIG. 5 is a pixel circuit diagram illustrating a single X-ray detector according to a third embodiment of the present disclosure.

FIG. 5 is a circuit diagram illustrating a single X-ray detector according to a third embodiment of the present disclosure.

Referring to FIG. 5, in accordance with the third embodiment of the present disclosure, a single X-ray detector 130 may include a first thin film transistor TFT1, a second thin film transistor TFT2, a first photodiode PD1 and a second photodiode PD2 in a single image pixel. Although the first thin film transistor TFT1 and the second thin film transistor TFT2 may have the same electrical characteristics, they may have different electrical characteristics. Although the first photodiode PD1 and the second photodiode PD2 may have the same photoelectric characteristics, they may have different photoelectric characteristics in this embodiment.

In this embodiment, the single pixel as described above may be included in an X-ray detecting panel of the X-ray detector 130, and may detect X-rays and output a signal.

For example, each of the first thin film transistor TFT1 and the second thin film transistor TFT2 may be configured to have a different channel resistance, a different on-current, a different off-current, a different channel length, a different channel width, and a different threshold voltage so as to process signals. The first photodiode PD1 and the second photodiode PD2 may be formed of different materials or thicknesses each other so as to generate an electrical signal from radiated light, or may be configured to have different fill factors. In this case, a PIN diode, an avalanche photo diode APD, or the like may be respectively used as the photodiodes PD1 and PD2 in this embodiment.

In this embodiment, each of the first photodiode PD1 and the second photodiode PD2 is electrically connected to a bias line at one side. The other side of the first photodiode PD1 may be electrically connected to a source terminal of the first thin film transistor TFT1. A gate terminal of the first thin film transistor TFT1 may be electrically connected to a gate line, and a drain terminal of the first thin film transistor TFT1 may be electrically connected to a first readout line Readout1.

The other side of the second photodiode PD2 may be electrically connected to a source terminal of the second thin film transistor TFT2. A gate terminal of the second thin film transistor TFT2 may be electrically connected to the gate line, and a drain terminal of the second thin film transistor TFT2 may be electrically connected to a second readout Readout2.

Figure 6:
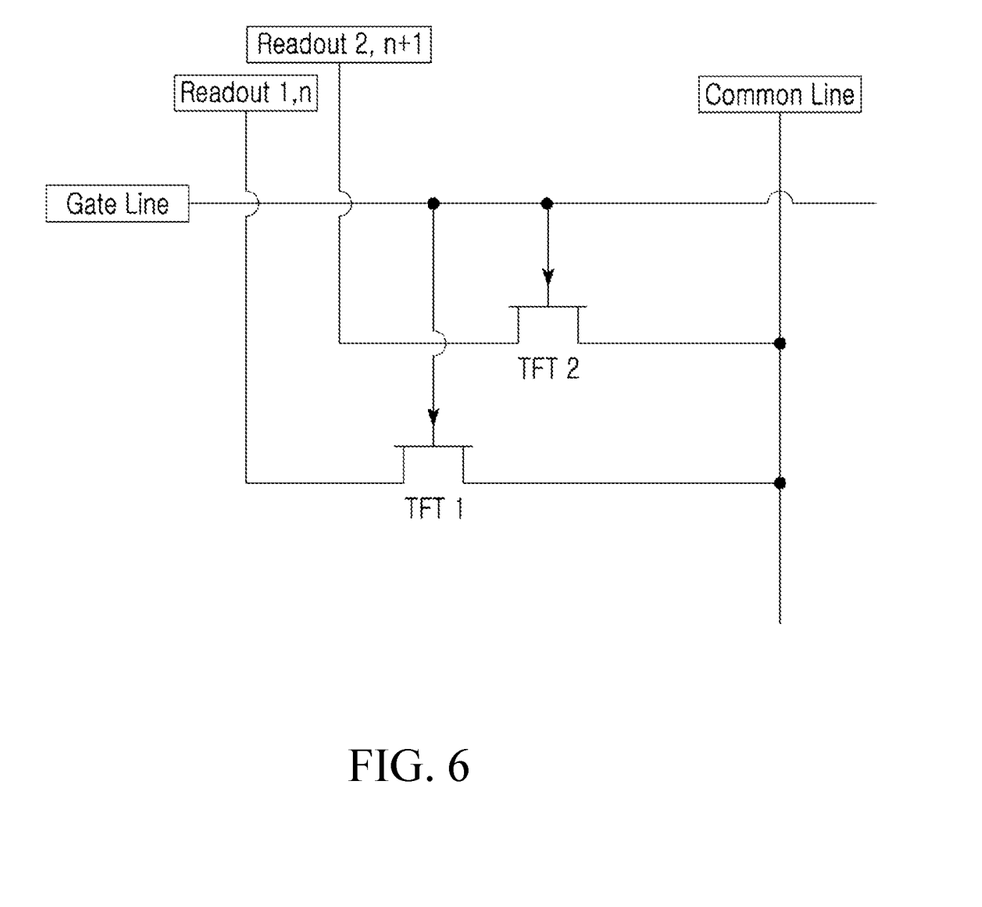
FIG. 6 is a pixel circuit diagram illustrating a single X-ray detector according to a fourth embodiment of the present disclosure.

FIG. 6 is a circuit diagram illustrating a single X-ray detector according to a fourth embodiment of the present disclosure.

Referring to FIG. 6, in accordance with the fourth embodiment of the present disclosure, a single X-ray detector 130 may include two thin film transistors TFT1 and TFT2 in a single unit pixel. In this embodiment, the two thin film transistors TFT1 and TFT2 may be applied to an X-ray detecting panel for directly detecting X-rays as an electrical signal. In this case, the unit pixel as described above may be included in the X-ray detecting panel of the X-ray detector 130, and may output the signal by detecting the X-rays in this embodiment.

Two thin film transistors TFT1 and TFT2 directly process X-rays as the electrical signal. The two thin film transistors TFT1 and TFT2 may have the same electrical characteristics, but the present disclosure is not limited thereto, and may have different electrical characteristics each other.

For example, each of the first thin film transistor TFT1 and the second thin film transistor TFT2 may be configured to have a different channel resistance, a different on-current, a different off-current, a different channel length, a different channel width, and a different threshold voltage so as to process electrical signals owing to the X-rays.

In this embodiment, source terminals of the two thin film transistors TFT 1 and TFT 2 may be electrically connected to a common line in which the X-rays are processed as electrical signals. Gate terminals of the two thin film transistors TFT1 and TFT2 may be connected to a gate line and drain terminals of the two thin film transistors TFT1 and TFT2 may be connected to two readouts Readout1 and Readout2, respectively.

Each of readout signals generated in the two thin film transistors TFT1 and TFT2 may be extracted through a readout terminal and may be realized as an image through an external electronic device connected to the readout terminal.

In this embodiment, the X-rays emitted from the X-ray source 110 are detected as electrical signals, and then the detected electrical signals are processed by the two thin film transistors TFT1 and TFT2 through the common line using their respective electrical characteristics, thereby realizing different images each other. Therefore, even when the same X-rays are radiated to the object 140 using one X-ray source 110, it is possible to realize an image having a sharper contrast with respect to the object 140 since the electric characteristics processed by the two thin film transistors TFT1 and TFT2 are different.

In this embodiment, although two thin film transistors TFT1 and TFT2 are used, more thin film transistors may be included in one pixel if necessary.

Although some exemplary embodiments have been described herein, it should be understood by those skilled in the art that these embodiments are given by way of illustration only, and that various modifications, variations, and alterations can be made without departing from the spirit and scope of the present disclosure. Therefore, the scope of the present disclosure should be limited only by the accompanying claims and equivalents thereof.

I claim:

1. An X-ray detecting panel for multi signal detection comprising a plurality of unit pixels,
   the unit pixel comprising:
   at least one photodiode generating an electrical signal by radiated light; and
   at least two thin film transistors processing the electrical signal generated in the at least one photodiode,
   wherein the at least two thin film transistors have different electrical characteristics from each other.

2. The X-ray detecting panel for multi signal detection of claim 1,
   wherein the unit pixel comprises at least two photodiodes having different photoelectric characteristics from each other.

3. The X-ray detecting panel for multi signal detection of claim 2,
   wherein the at least two photodiodes have different materials and thicknesses from each other, or have different fill factors from each other.

4. The X-ray detecting panel for multi signal detection of claim 2,
   wherein the at least two thin film transistors are configured to have different channel resistances, on-currents, off-currents, channel lengths, channel widths, or threshold voltages from each other.

5. The X-ray detecting panel for multi signal detection of claim 2,
   wherein one sides of the at least two photodiodes are electrically connected to a bias line, and other sides of the at least two photodiodes are electrically connected to source terminals of the at least two thin film transistors, respectively, and
   wherein drain terminals of the at least two thin film transistors are connected to at least two readouts so as to output a signal generated in each of the at least two photodiodes as image information.

6. The X-ray detecting panel for multi signal detection of claim 1,
   wherein the at least two thin film transistors are configured to have different channel resistances, on-currents, off-currents, channel lengths, channel widths, or threshold voltages from each other.

7. The X-ray detecting panel for multi signal detection of claim 1,
   wherein the unit pixel comprises a single photodiode,
   the photodiode having one side electrically connected to a bias line and the other side electrically connected to source terminals of the at least two thin films transistors, and
   wherein drain terminals of the at least two thin film transistors are connected to at least two readouts so as to output signals generated in the photodiode as image information.

8. An X-ray detecting panel for multi signal detection comprising a plurality of unit pixels,
   the unit pixel comprising:
   at least two photodiodes each generating an electrical signal by radiated light; and a single thin film transistor processing the electrical signals generated in the at least two photodiodes, wherein the at least two photodiodes have different photoelectric characteristics from each other, wherein each of the at least two photodiodes is electrically connected to a bias line at one side and electrically connected to a source terminal of the single thin film transistor at the other side, and wherein a drain terminal of the single thin film transistor is connected to a readout.

9. An X-ray detecting panel for multi signal detection comprising a plurality of unit pixels, the unit pixel comprising:

a first thin film transistor directly detecting radiated X-rays as an electrical signal and processing the detected electrical signal; and a second thin film transistor directly detecting the radiated X-rays as an electrical signal and processing the detected electrical signal, wherein the first and second thin film transistors have different electrical characteristics from each other.

10. The X-ray detecting panel for multi signal detection of claim 9, wherein the first and second thin film transistors are configured to have different channel resistances, on-currents, off-currents, channel lengths, channel widths, or threshold voltages from each other.

11. The X-ray detecting panel for multi signal detection of claim 9, wherein source terminals of the first and second thin film transistors are electrically connected to a common line where X-rays are detected as electrical signals, and wherein drain terminals of the first and second thin film transistors are connected to first and second readouts to output electrical signals as which X-rays are detected as image information.

12. An X-ray detector for multi signal detection, comprising:

an X-ray detecting panel for multi signal detection comprising a plurality of unit pixels, the unit pixel comprising:

at least one photodiode generating an electrical signal by radiated light; and at least two thin film transistors processing the electrical signal generated in the at least one photodiode, and wherein the at least two thin film transistors have different electrical characteristics from each other.

13. The X-ray detector for multi signal detection of claim 12, wherein the unit pixel comprises at least two photodiodes having different photoelectric characteristics from each other.

14. The X-ray detector for multi signal detection of claim 13, wherein the at least two photodiodes have different materials and thicknesses from each other, or may have different fill factors from each other.

15. The X-ray detector for multi signal detection of claim 13, wherein one sides of the at least two photodiodes are electrically connected to a bias line, and other sides of the photodiodes are electrically connected to source terminals of the at least two thin film transistors, respectively, and wherein drain terminals of the at least two thin film transistors are connected to a plurality of readouts so as to output a signal generated in each of the at least two photodiodes as image information.

16. The X-ray detector for multi signal detection of claim 12, wherein the at least two thin film transistors are configured to have different channel resistances, on-currents, off-currents, channel lengths, channel widths, or threshold voltages, respectively.

17. An X-ray detector for multi signal detection comprising:

an X-ray detecting panel for multi signal detection comprising a plurality of unit pixels, the unit pixel comprising:

a first thin film transistor directly detecting radiated X-rays as an electrical signal and processing the detected electrical signal; and a second thin film transistor directly detecting the radiated X-rays as an electrical signal and processing the detected electrical signal, wherein the first and second thin film transistors have different electrical characteristics from each other.

* * * * *